United States Patent [19]

Wang et al.

[11] Patent Number: 5,304,294
[45] Date of Patent: Apr. 19, 1994

[54] METHOD AND APPARATUS FOR SENSING NOX

[75] Inventors: Da Y. Wang, Lexington; Daniel T. Kennedy, Burlington, both of Mass.; Burton W. MacAllister, Jr., Hudson, N.H.

[73] Assignee: GTE Laboratories Incorporated, Waltham, Mass.

[21] Appl. No.: 974,051

[22] Filed: Nov. 10, 1992

Related U.S. Application Data

[62] Division of Ser. No. 843,877, Feb. 27, 1992, Pat. No. 5,217,588.

[51] Int. Cl.$^5$ .............................. G01N 27/26
[52] U.S. Cl. ........................ 204/426; 204/427; 204/424
[58] Field of Search ............... 204/424, 425, 426, 427, 204/428, 429

[56] References Cited

U.S. PATENT DOCUMENTS

| | | | |
|---|---|---|---|
| 2,773,237 | 12/1956 | Offut et al. | 324/31 |
| 4,450,065 | 5/1984 | Yamada et al. | 204/412 |
| 4,722,779 | 2/1988 | Yamada et al. | 204/426 |
| 4,769,124 | 9/1988 | Okada et al. | 204/425 |
| 4,770,760 | 9/1988 | Noda et al. | 204/426 |
| 4,816,749 | 3/1989 | Schmidtpott et al. | 324/711 |
| 4,880,519 | 11/1989 | Wang et al. | 204/425 |
| 4,909,072 | 3/1990 | Logothetis et al. | 73/116 |
| 5,034,107 | 7/1991 | Wang et al. | 204/153.14 |
| 5,080,765 | 1/1992 | Wang et al. | 204/426 |

FOREIGN PATENT DOCUMENTS 0257842 3/1988 European Pat. Off.

OTHER PUBLICATIONS

Wang et al., Presentation and Publication in Proceedings, 93rd Annual Mtg. Symposium on Point Defects and Related Properties of Ceramics, Cinncinnati, Ohio, Apr. 28-May 2, 1991.

Soviet Inventions Illustrated: Section E1: Electrical Week 8343, Dec. 7, 1983, Instrumentation, Measuring and Testing-p. 6, 83-799823/43, SU-983-828-A.

R. Kaiser, Chromatographie in der Gasphase: I. Gas--Chromatographie, pp. 189-200, Hochschultaschenbucher Bibliographisches Institut.

*Primary Examiner*—John Niebling
*Assistant Examiner*—Bruce F. Bell
*Attorney, Agent, or Firm*—Victor F. Lohmann, III

[57] ABSTRACT

Apparatus and method for determining the concentration of NOx in a gas mixture. The gas mixture is supplied to two electrodes at which different NOx decomposition conditions are present. The electrodes may be of different materials or sizes or may be positioned in different gas enclosure environments. The NOx decomposes at different rates at the two electrodes and an emf is thus produced between the electrodes. The concentration of NOx in the gas mixture is determined from the measured emf.

7 Claims, 9 Drawing Sheets

METHOD AND APPARATUS FOR SENSING NOX

This is a divisional continuation of copending application Ser. No. 07/843,877 filed on Feb. 27, 1992, now U.S. Pat. No. 5,217,588.

This invention is related to subject matter disclosed in application Ser. No. 490,812, filed Mar. 8, 1990 now U.S. Pat. NO. 5,100742 by Da Yu Wang, Daniel T. Kennedy, and Burton W. MacAllister Jr., and entitled "A Method and Device for Gaseous Fuel Cell Operation."

BACKGROUND OF THE INVENTION

This invention relates to gas sensing. More particularly, it is concerned with methods and apparatus for measuring the concentration of NOx (oxides of nitrogen such as $N_2O$, NO, $NO_2$) in a gas mixture.

Various techniques and apparatus have been developed for determining the concentration of NOx in a gas mixture, particularly gas mixtures including oxygen and nitrogen. Typically the electrochemical sensing of NOx and other gases has been based on the oxygen pumping principle, for example, as described in U.S. Pat. No. 4,770,760 to Noda et al. and U.S. Pat. No. 5,034,107 to Wang et al. The sensing apparatus employed require two sensing elements. One element senses only oxygen gas and the other element senses all the gases which contain oxygen, including the oxygen gas. Both sensing elements are exposed to the same gas mixture, and the difference between the sensing signals produced by these two elements is a measure of the concentration of NOx in the gas mixture. Since the NOx concentration is determined from the difference between two signals, the accuracy of measurement is determined by the relative values of the two signals. If the gas mixture contains a relatively low NOx concentration as compared with that of oxygen, the signal-to-noise ratio is small and an accurate determination of the NOx concentration is difficult.

SUMMARY OF THE INVENTION

The method of determining the concentration of NOx in a gas in accordance with the present invention comprises providing an electrolyte sensor having a first electrode and a second electrode. A different NOx decomposition condition is present at each of the electrodes. Both electrodes are exposed to a test gas, and the electrical differential between the two electrodes is measured. The concentration of NOx in the test gas is determined from the measured electrical differential.

NOx-sensing apparatus in accordance with the present invention comprises a body of an electrolyte material. First and second electrodes are attached to the body. A different NOx decomposition condition is present at each of the electrodes. Means are provided for measuring the electrical differential between the two electrodes when the electrodes are exposed to a test gas.

The sensing principle employed in the present invention is that the NOx gases are not stable and readily decompose into oxygen and nitrogen. When nonsymmetrical decomposition conditions exist at two electrodes in a solid oxide electrolyte device, oxygen activities at the electrodes differ even though both electrodes are exposed to the same gas. Therefore, an electromotive force is produced between the two electrodes, and the value of that electromotive force can be utilized to determine the concentration of NOx in the gas.

For a better understanding of the present invention, together with other and further objects, advantages, and capabilities thereof, reference is made to the following disclosure and appended claims in connection with the above-described drawings.

DETAILED DESCRIPTION

NOx gases are not stable and readily decompose into oxygen and nitrogen. When nonsymmetrical conditions involving the NOx decomposition process are present at two different electrodes, an electromotive force occurs between the two electrodes. That is, by virtue of different NOx decomposition rates at the electrodes, the oxygen activity at the electrodes is different and this difference is measurable as an electromotive force. The decomposition conditions may be nonsymmetrical in catalytic effect by virtue of the electrodes being of different materials, which materials have different catalytic decomposition rates for NOx. Alternatively, the two electrodes may be of different size. In other embodiments in accordance with the present invention, the two electrodes are located in different gas enclosure environments such that NOx decomposition conditions are different at each of the electrodes.

Figure 1:
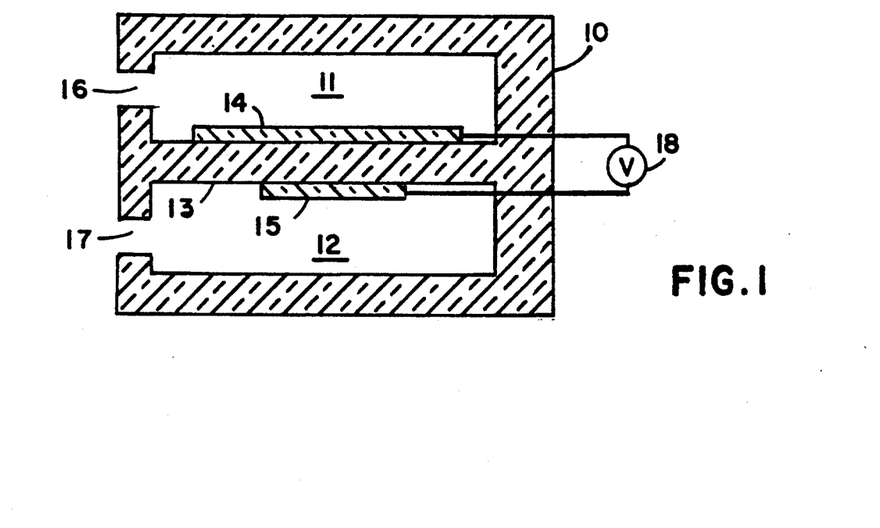
FIGS. 1, 2, 3, 4 and 5 illustrate in cross-section various embodiments of NOx-sensing apparatus in accordance with the present invention.

FIG. 1 illustrates in cross-section a sensing device having a body 10 which is of a solid oxide electrolyte such as, for example, yttria-stabilized zirconia or partially stabilized zorconia. The sensor body 10 forms two chambers 11 and 12 with a wall 13 between the two chambers. Both chambers 11 and 12 are of the same size and shape. A first electrode 14 of platinum and a second electrode 15 of platinum are attached to the wall 13 on opposite sides in chambers 11 and 12, respectively. Under operating conditions a gas mixture containing NOx is introduced into both chambers 11 and 12 through identical apertures 16 and 17, respectively. The NOx decomposes into nitrogen and oxygen at the electrodes. As illustrated in FIG. 1, electrode 14 is larger than electrode 15; and, therefore, the oxygen activities in the electrodes are not the same. As a result a potential differential, or emf, exists between the two electrodes 14 and 15 and may be measured by a suitable voltage measuring device 18.

The electrodes 14 and 15 may be of materials which provide different catalytic-decomposition rates for NOx. For example, one may be of platinum and the other of rhodium. With dissimilar materials the electrodes 14 and 15 may be of the same size. In any event, nonsymmetrical decomposition conditions for NOx are provided at the electrodes so as to produce a potential differential which may be measured and the measurement employed to determine the concentration of NOx in the gas introduced into the chambers.

Figure 2:
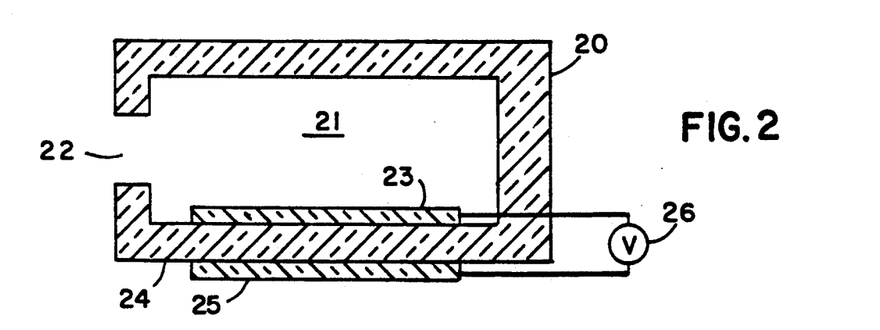

FIG. 2 illustrates in cross-section a sensing device in accordance with the present invention having a body 20 of a solid oxide electrolyte forming a single chamber 21 having an aperture 22. A first electrode 23 is mounted on a wall 24 of the body interior of the chamber 21 and a similar electrode 25 is mounted on the body 20 exterior of the chamber 21 and directly opposite the first electrode 23. When the device is exposed to a gas containing NOx, the NOx within the chamber 21 decomposes at a rate different from that externally of the chamber since the gas enclosure environments are different. As can be seen, the oxygen from the decomposed NOx is freer to move away from the electrode externally of the chamber than from the electrode 23 within the chamber. Thus, an emf is generated between the electrodes. The emf is measured by a suitable potential measuring device 26 and used to determine the concentration of NOx in the gas.

Figure 3:
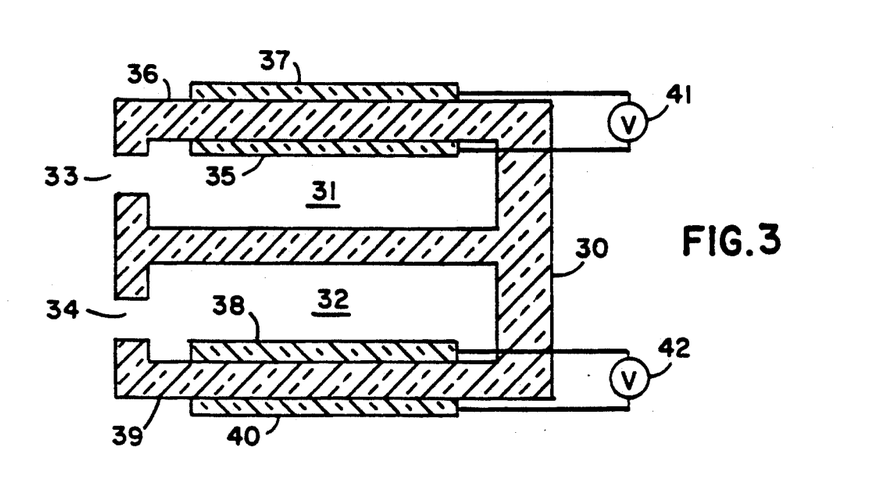

FIG. 3 illustrates another embodiment of a sensing device in accordance with the present invention having a solid oxide electrolyte body 30 forming two chambers 31 and with apertures 33 and 34 providing passage thereto, respectively. An electrode 35 is mounted inside the chamber on a wall 36 with another electrode 37 mounted opposite the electrode 35 but externally of the device. Similarly, an electrode 38 is mounted within the chamber 32 on a wall 9 and an opposing electrode 40 is mounted on wall 39 externally of the chamber 32. The emf produced between electrodes 35 and 37 is measured by a voltage meter 41 and that between electrodes 38 and 40 by a voltage meter 42. In the particular structure, as will be discussed hereinbelow, the chambers 31 and 32 may be of different sizes and/or the apertures 33 and 34 may be of different sizes. In effect, the device of FIG. 3 is two sensors in accordance with FIG. 2 in a unitary structure. The differences in the chambers and/or the apertures provide two different sets of NOx decomposition conditions.

Figure 4:
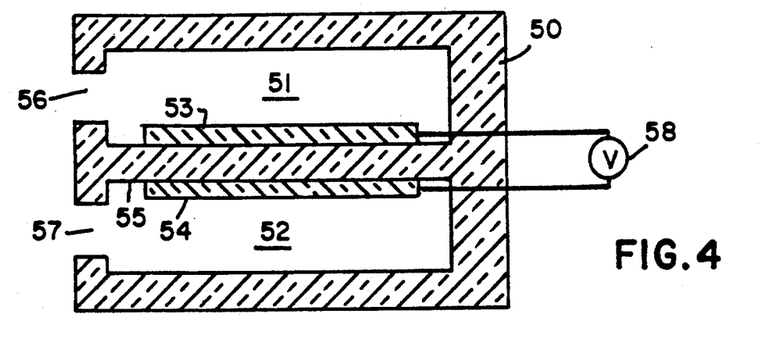

FIG. 4 illustrates a device with a body 50 of solid oxide electrolyte divided into two chambers 51 and 52. Electrodes 53 and 54 are mounted in opposition on opposite sides of a wall 55 which separates the two chambers 51 and 52. The chambers 51 and 52 have apertures 56 and 57, respectively. The device functions by providing different gas enclosure environments for the electrodes 53 and 54. The environments are different by virtue of the sizes of chambers 51 and 52 being different and/or by the sizes of the apertures 56 and 57 being different. The emf produced between the two electrodes 53 and 54 is measured by a voltage measuring device 58.

Figure 5:
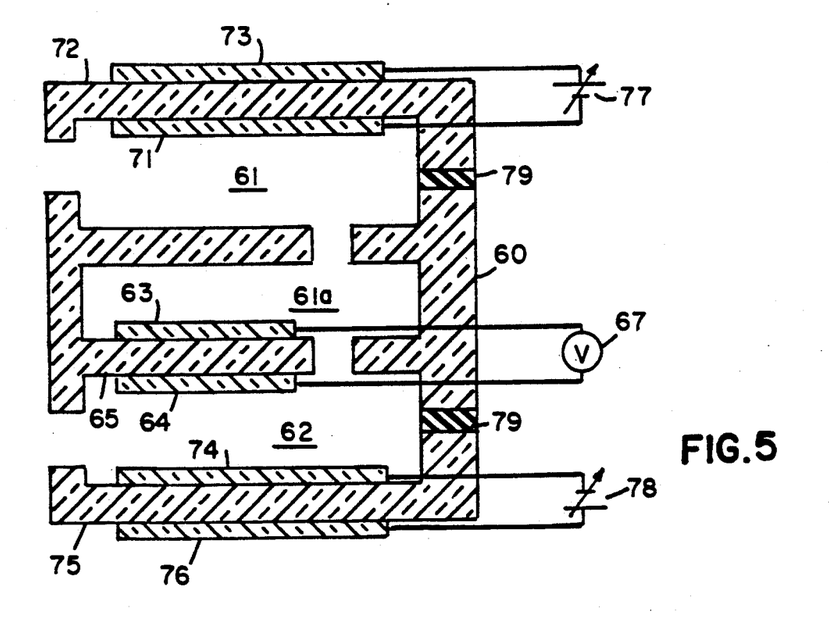

FIG. 5 illustrates another embodiment of a NOx-sensing device in accordance with the present invention. The body of the device 60 is of a solid oxide electrolyte. The body is formed into essentially two chambers 61 and 62 with a passage from chamber 61 into an inner portion thereof 61a. Platinum electrodes 63 and 64 are mounted on wall 65 of the body between the two chambers 61a and 62. As illustrated, there is also a passage between the chambers 61a and 62. The configuration of the chambers 61, 61a, 62 and the various apertures and passages are such as to ensure that electrodes 63 and 64 are exposed to different gas enclosure environments. Thus, the presence of a NOx-containing gas causes a measurable emf to be generated across the electrodes 63 and 64 and detected by a voltage measuring device 67.

The apparatus of FIG. 5 also includes an electrode 71 within chamber 61 on outside wall 72 with an opposing electrode 73 mounted externally on wall 72. An electrode 74 is mounted within chamber 62 on exterior wall 75. Another electrode 76 is mounted externally of the device opposite electrode 74. Electrodes 71 and 73 are connected across a voltage source 77 and electrodes 74 and 76 are connected across a voltage source 78.

The arrangement of electrodes 71 and 73 across the solid electrolyte wall 72 provides a pumping cell for pumping oxygen out of chamber 61. Similarly, the electrodes 74 and 76 and the intervening solid electrolyte wall 75 provide a pumping cell for pumping oxygen out of chamber 62. The two pumping cells are electrically isolated from the sensing cell by suitable insulating material 79. The sensing device of FIG. 5 enables small amounts of NOx to be detected in gas mixtures containing high levels of oxygen. Reducing the amount of oxygen in the chamber increases the sensitivity of the device to the effects of NOx decomposition.

A sensing device of the general nature as illustrated in FIG. 3 was fabricated employing thick film, multilayer technology as discussed in detail in U.S. Pat. No. 4,880,519 to Wang et al. Each of the gas chambers 31 and 32 had a diameter of 4.3 millimeters and a height of 0.16 millimeter. The thickness of the solid electrolyte walls 36 and 39 between the associated electrodes of each pair was 0.16 millimeter. The sizes of the orifices 33 and 34 were 50 micrometers and 180 micrometers, respectively, providing a size ratio of 3.6. The electrodes 35, 37, 38 and 40 were formed of screen-printed platinum ink and measured 15 millimeters$^2$.

The device as described was exposed to $N_2O/O_2/N_2$ mixtures of various composition. Table 1 is test data obtained from the two sets of electrodes. The temperature was 574° C.

TABLE 1

| $N_2O$ % | $O_2$ % | 1st emf (mV) | 2nd emf (mV) |
|---|---|---|---|
| 0.000 | 20.970 | −0.600 | 0.410 |
| 6.443 | 19.619 | −0.090 | 0.820 |
| 12.271 | 18.397 | 1.290 | 1.950 |
| 17.511 | 17.298 | 2.520 | 2.910 |
| 22.118 | 16.332 | 3.670 | 3.800 |
| 26.083 | 15.500 | 5.010 | 4.860 |
| 29.734 | 14.735 | 5.580 | 5.270 |
| 33.073 | 14.035 | 6.570 | 6.010 |
| 36.138 | 13.392 | 7.570 | 6.800 |
| 39.381 | 12.712 | 8.670 | 7.630 |
| 56.990 | 9.030 | 13.660 | 11.800 |
| 72.750 | 5.720 | 17.930 | 14.010 |
| 99.900 | 0.000 | 24.510 | 17.950 |

Figure 6:
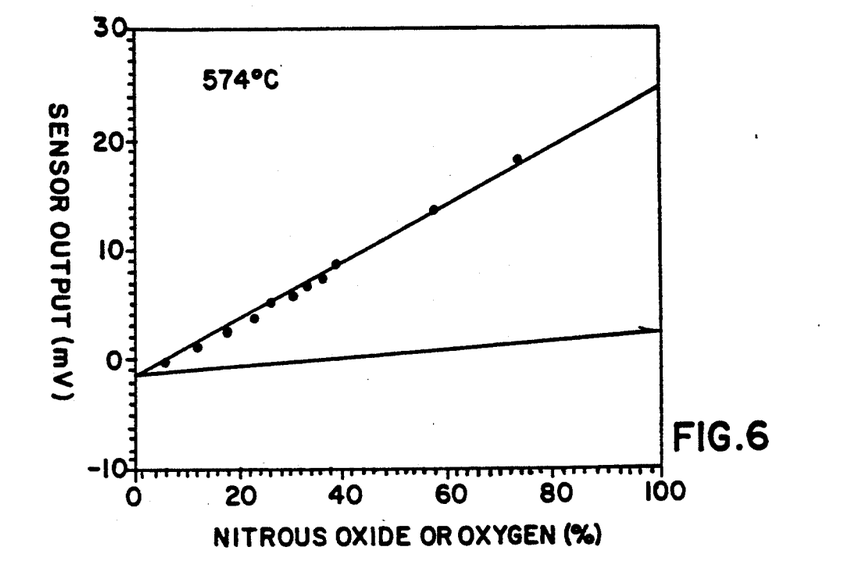
FIGS. 6-13 are graphs displaying output signals versus NOx concentration for various NOx-sensing apparatus in accordance with the invention under different conditions.

FIG. 6 is a plot of the 1st emf data of Table 1. The solid line in FIG. 6 shows the emf output obtained when $N_2O$ was replaced with $O_2$ and there was no decomposition of $N_2O$ included.

The effect on the emf by the decomposition of NOx can be enhanced if the oxygen concentration at the electrodes is reduced. Table 2 is test data for gas mixtures of $N_2O/O_2/N_2$ with an oxygen level of 1%. The temperature was 523° C. For the data in Table 3, the oxygen concentration was 140 ppm (parts per million) and the temperature was 516° C.

TABLE 2

| $N_2O$ (ppm) | 1st emf (mV) | 2nd emf (mV) |
|---|---|---|
| 13.039 | −1.390 | −0.060 |
| 34.101 | −1.400 | −0.070 |
| 64.188 | −1.380 | −0.080 |
| 104.302 | −1.360 | −0.090 |
| 305.824 | −1.340 | −0.060 |
| 604.449 | −1.200 | 0.050 |
| 1002.004 | −0.880 | 0.290 |
| 2131.855 | −0.150 | 0.720 |
| 5664.818 | 1.560 | 2.080 |
| 8473.228 | 2.540 | 2.840 |
| 20234.082 | 6.020 | 5.380 |

TABLE 2-continued

| $N_2O$ (ppm) | 1st emf (mV) | 2nd emf (mV) |
|---|---|---|
| 40977.299 | 10.290 | 8.420 |
| 65858.389 | 13.700 | 10.780 |
| 124670.764 | 18.650 | 14.090 |
| 176033.058 | 21.420 | 15.980 |
| 262573.964 | 24.480 | 18.130 |
| 415934.388 | 28.400 | 20.620 |

TABLE 3

| $N_2O$ (ppm) | 1st emf (mV) | 2nd emf (mV) |
|---|---|---|
| 78.329 | 1.150 | −0.850 |
| 213.595 | 1.300 | −0.680 |
| 427.099 | 1.900 | −0.220 |
| 711.630 | 2.800 | 0.500 |
| 2131.855 | 6.680 | 3.690 |
| 4254.639 | 8.530 | 5.140 |
| 7071.009 | 10.640 | 6.850 |
| 20917.215 | 14.960 | 10.020 |
| 40977.299 | 19.410 | 13.290 |
| 66749.401 | 21.500 | 14.950 |

Figure 7:
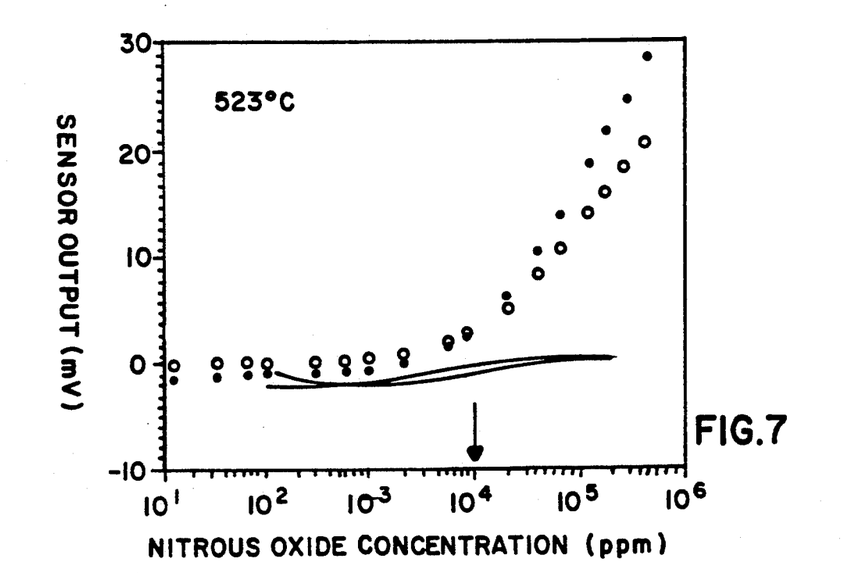
Figure 8:
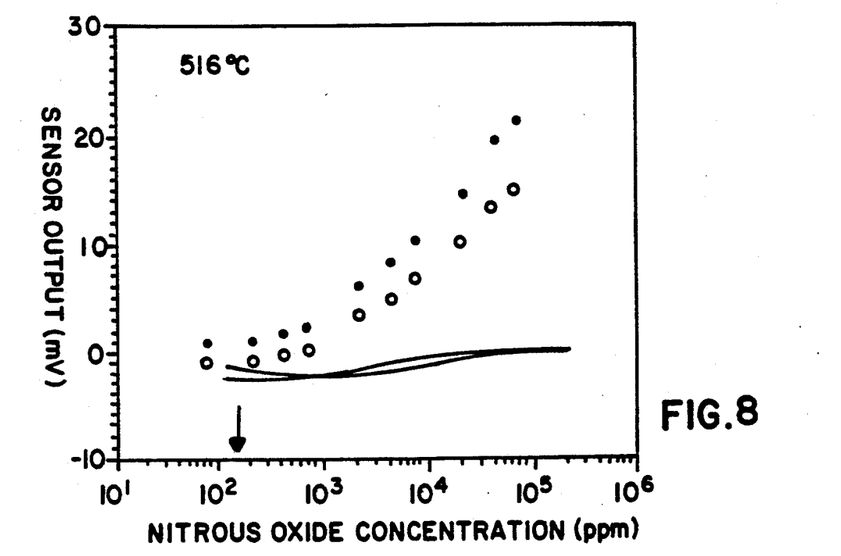
Figure 9A:
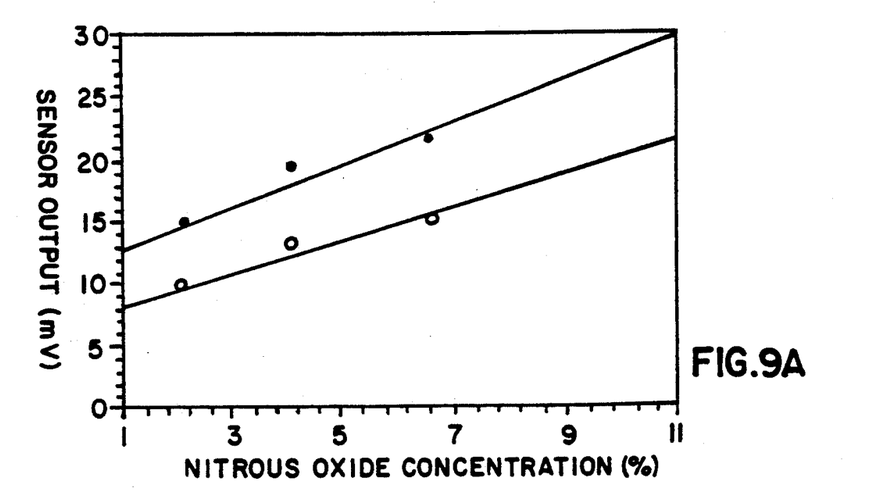
Figure 9B:
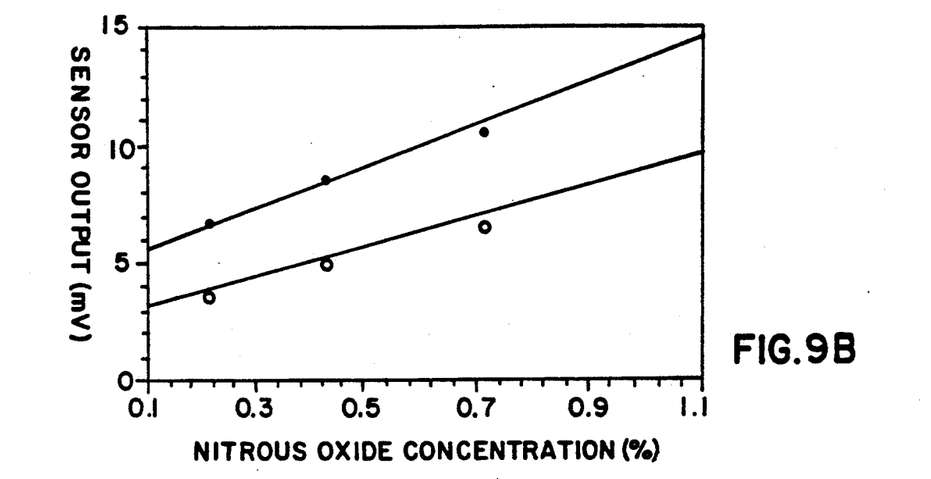
Figure 9C:
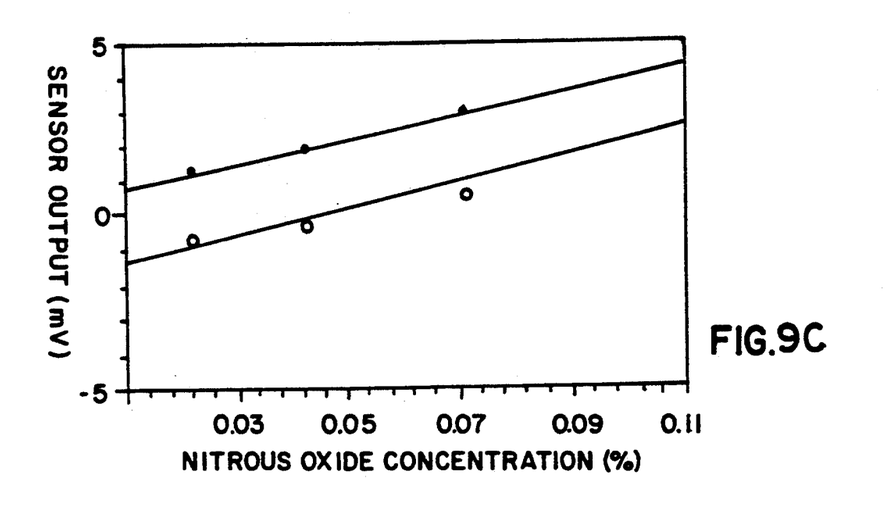

FIG. 7 is a plot of both columns of emf data from Table 2 with the arrow indicating the oxygen concentration level. FIG. 8 is a plot of both columns of emf data from Table 3 with the arrow indicating the oxygen concentration level. The solid lines on the graphs of FIG. 7 and FIG. 8 indicate the measured emfs when the $N_2O$ was replaced with oxygen. FIGS. 9A, 9B, and 9C are linear plots from the data in Table 3 and FIG. 8 showing the relationship of the sensor output voltage versus the $NO_2$ concentration as a percentage of the gas mixture.

Figure 10:
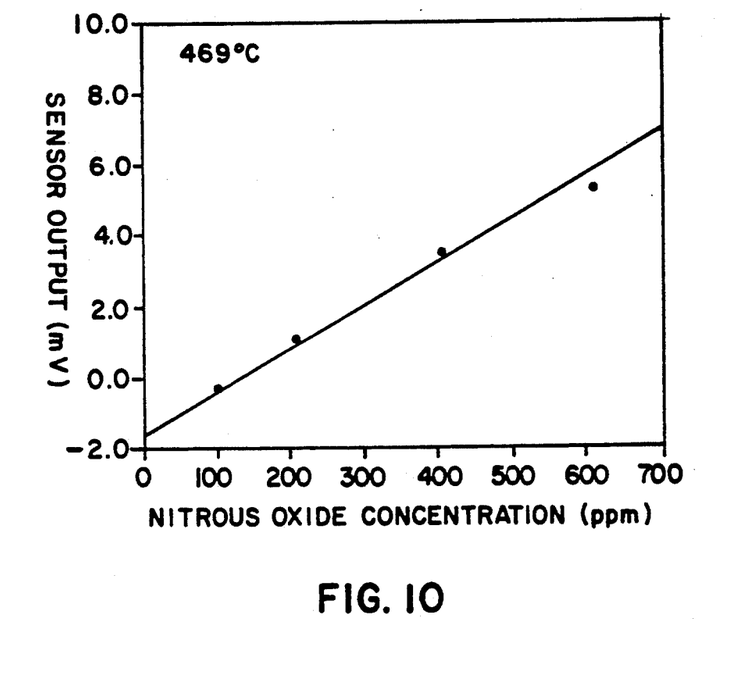

FIG. 10 is a plot of data obtained from using a single set of emf data produced under conditions of 469° C. with an oxygen concentration of 20 ppm. In comparison with the other data, this plot illustrates the manner in which the output level changes with oxygen concentration and operating temperature.

A device as illustrated in FIG. 2 was fabricated employing yttria-stabilized zirconia with a chamber 21 having a diameter of 4.3 millimeters and a height of 0.16 millimeters. The thickness of the wall 24 between the two electrodes 23 and 25 was also 0.16 millimeter. The aperture was 50 micrometers. The electrodes 23 and 25 were screen-printed platinum ink and were 15 millimeters$^2$. Test data with the device operating at 462° C. is shown in Table 4.

TABLE 4

| $N_2O$ (ppm) | Emf (mV) |
|---|---|
| 71 | 0.700 |
| 213.4 | 1.960 |
| 498 | 3.800 |
| 711 | 5.200 |
| 1421 | 8.300 |
| 2130 | 10.800 |
| 4955 | 16.300 |
| 7064 | 19.120 |
| 20900 | 25.000 |
| 47400 | 28.300 |
| 66400 | 28.400 |

Figure 11A:
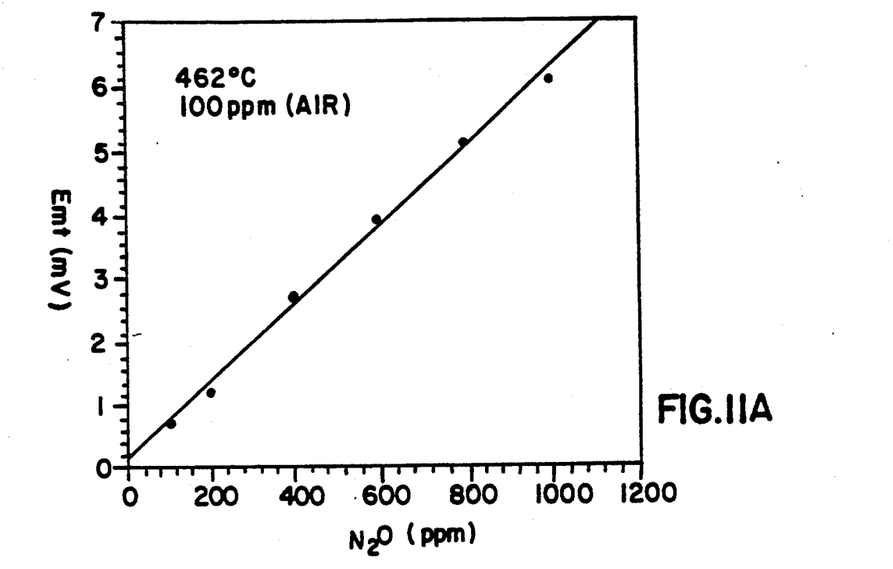
Figure 11B:
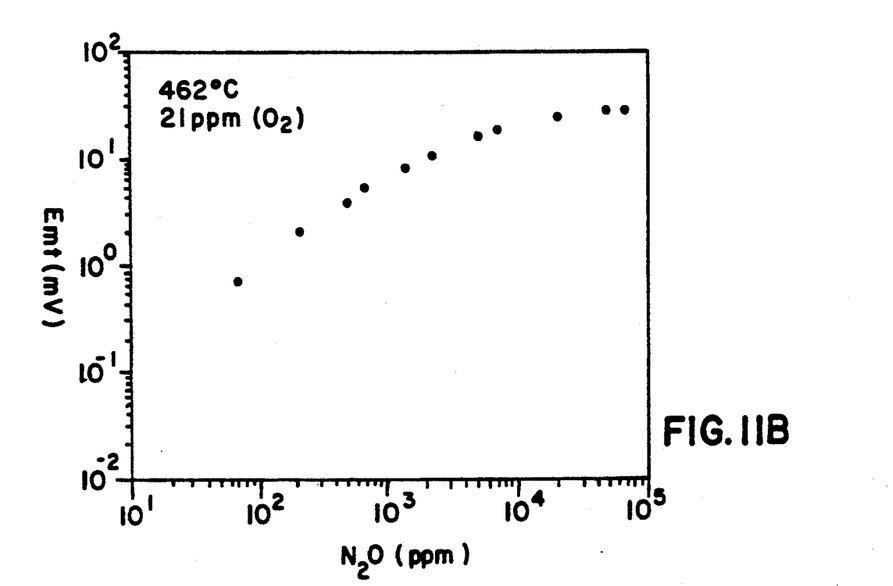

FIGS. 11A and 11B are plots of the data of Table 4.

Figure 12:
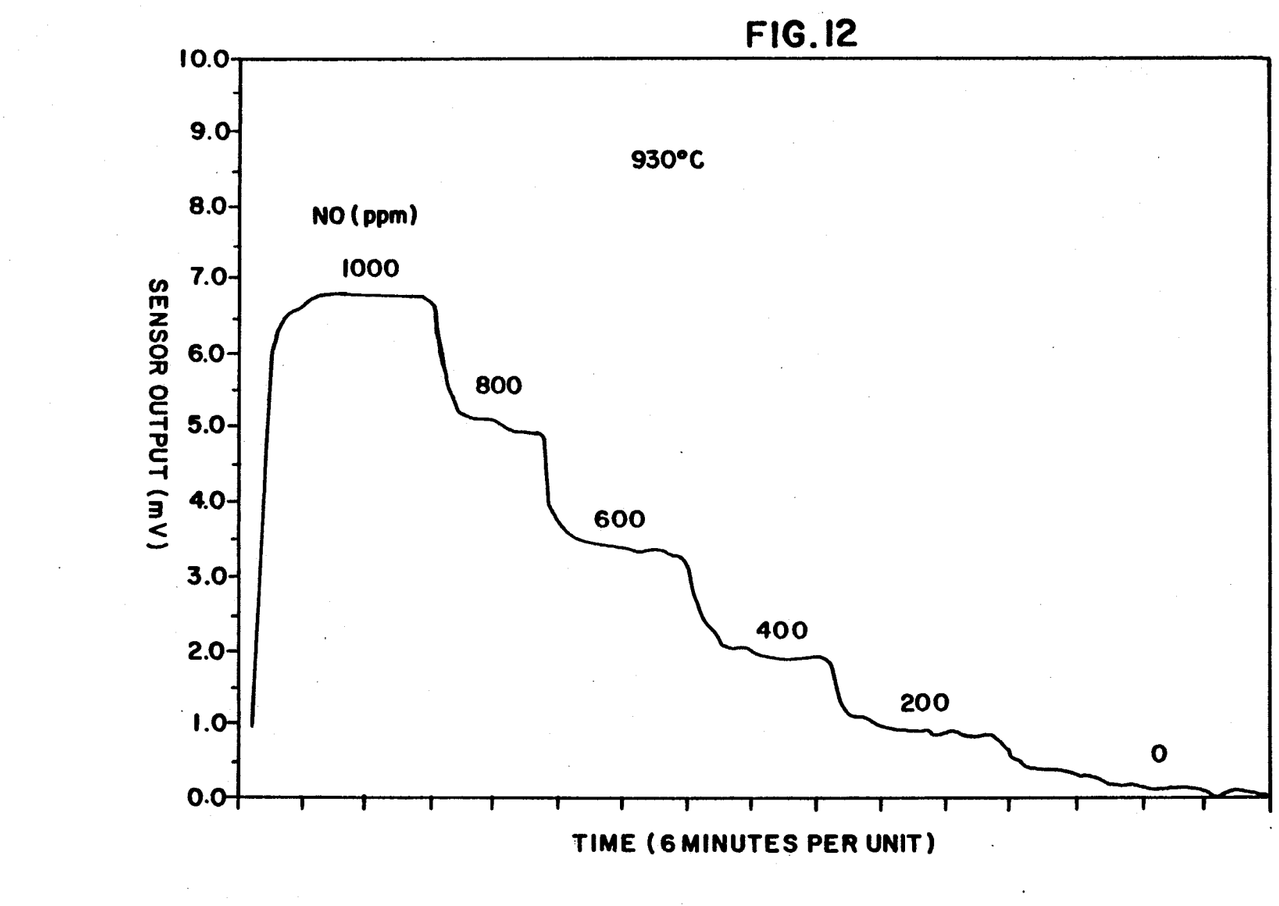

A device as illustrated in FIG. 2 was fabricated employing yttria-stabilized zirconia with a chamber 21 having a diameter of 4.3 millimeters and a height of 0.16 millimeters. The thickness of the wall 24 between the two electrodes 23 and 25 was also 0.16 millimeters. The aperture was 125 micrometers. The electrodes 23 and 25 were a screen-printed platinum ink of 15 millimeter$^2$ dimensions. Test data with the device operating at 930° C. in $NO/N_2/O_2$ gas mixture is given in FIG. 12, which shows the sensor output vs the time the sensor was exposed to the gas. Output signals vs the change of NO are listed in Table 5.

TABLE 5

| NO (ppm) | emf (mV) |
|---|---|
| 0 | 0.1 |
| 200 | 0.85 |
| 400 | 1.9 |
| 600 | 3.35 |
| 800 | 4.90 |
| 1000 | 6.80 |

The oxygen concentration in the gas mixture was 50 ppm.

Figure 13:
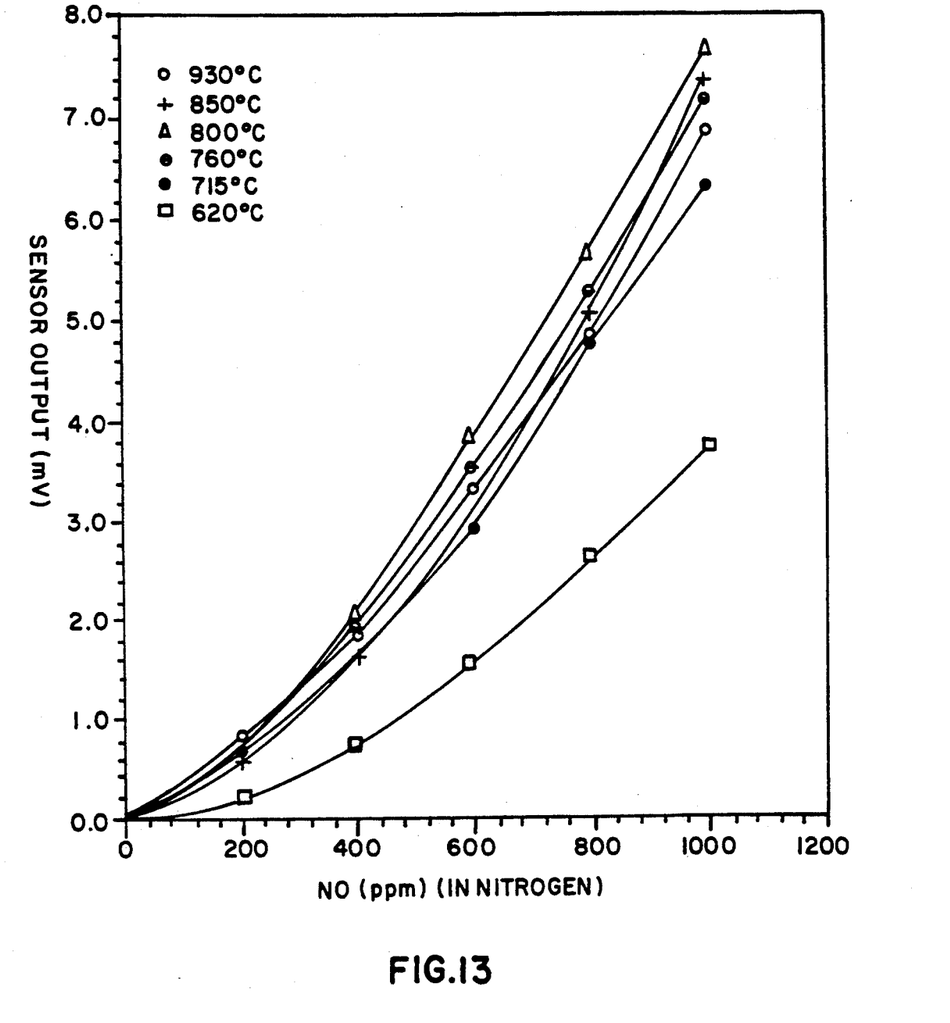

FIG. 13 shows the signal output data of the same sensor at six different temperatures, 620° C., 726° C., 760° C., 800° C., 850° C., and 930° C.

Although the specific solid oxide electrolyte employed was yttria-stabilized zirconia, other well-known oxygen anion conducting materials may be used such as calcium- or yttrium-doped ceria or magnesium- or calcium-doped zirconia. The device may be fabricated by employing techniques as described U.S. Pat. No. 5,034,107 or by other techniques which may be suitable. The electrodes may be other than platinum, such as palladium, platinum/palladium alloy, platinum/palladium composite, rhodium, or silver or gold and their alloys. As is well understood, the electrodes can be applied by screen printing or vapor deposition techniques. The sensed output signal can be the emf as described, or alternatively the electrical current generated by shorting the electrodes may be measured.

The devices as illustrated provide a simple, uncomplicated, and direct method and apparatus for measuring the concentration of NOx in an ambient gas by measuring the electrical differential generated by the decomposition of the NOx into nitrogen and oxygen under different decomposition conditions existing at the electrodes.

While there has been shown and described what are considered preferred embodiments of the present invention, it will be obvious to those skilled in the art that various changes and modifications may be made therein without departing from the invention as defined by the appended claims.

What is claimed is:

1. NOx-sensing apparatus comprising
   a body of an electrolyte material;
   a first electrode attached to said body;
   a second electrode attached to said body;
   said first and second electrodes having different $NO_x$ decomposition characteristics; and
   means for measuring the electrical differential between the two electrodes when the electrodes are exposed to a test gas.

2. NOx-sensing apparatus in accordance with claim 1 wherein said first and second electrodes are of different sizes.

3. NOx-sensing apparatus in accordance with claim 1 wherein said first and second electrodes are of materials having different NOx decomposition properties.

4. NOx-sensing apparatus comprising
   a body of an electrolyte material providing two different gas enclosure environments;
   a first electrode attached to said body in one a second electrode attached to said body in the other environment; and means for measuring the potential differential between gas enclosure environments.

5. NOx-sensing apparatus in accordance with claim 4 wherein one of the gas enclosure environments encompasses a larger space than the other gas enclosure environment.

6. NOx-sensing apparatus in accordance with claim 4 wherein said body includes a passage for introducing the test gas to one of the gas enclosure environments which is smaller than the passage for introducing the test gas to the other gas enclosure environment.

7. NOx-sensing apparatus comprising a body of an electrolyte material having a first chamber and a second chamber forming different gas enclosure environments;

a first electrode attached to said body in the first chamber;

a second electrode attached to said body in the second chamber;

a third electrode attached to said body in the first chamber;

a fourth electrode attached to said body externally of the first chamber in opposition to said third electrode with a wall of said body interposed between;

a fifth electrode attached to said body in the second chamber;

a sixth electrode attached to said body externally of the second chamber in opposition to said fifth electrode with a wall of said body interposed between;

means for applying electrical potential between said third and fourth electrodes to provide a pumping cell for reducing the amount of oxygen in the first chamber;

means for applying electrical potential between said fifth and sixth electrodes to provide a pumping cell for reducing the amount of oxygen in the second chamber; and means for measuring the potential differential between the first and second electrodes when a test gas is introduced into both chambers.

* * * * *